United States Patent [19]
Fleming

[11] Patent Number: 5,356,370
[45] Date of Patent: Oct. 18, 1994

[54] ANTIFRICTION MECHANICAL JOINT FOR AN ORTHOPEDIC KNEE BRACE

[75] Inventor: Bruce Fleming, Pitt Meadows, Canada

[73] Assignee: Generation II Orthotics Inc., Richmond, Canada

[21] Appl. No.: 120,261

[22] Filed: Sep. 9, 1993

[51] Int. Cl.$^5$ .............................................. A61F 5/00
[52] U.S. Cl. ....................................... 602/16; 602/26; 403/82; 403/158; 403/163
[58] Field of Search ................... 602/5, 16, 26, 20, 23; 128/870, 882; 403/68, 70, 71, 82, 158, 161, 163

[56] References Cited

U.S. PATENT DOCUMENTS

| | | |
|---|---|---|
| 3,902,482 | 9/1975 | Taylor . |
| 4,379,463 | 4/1983 | Meier et al. .................. 602/26 X |
| 4,463,751 | 8/1984 | Bledsoe . |
| 4,632,098 | 12/1986 | Grundei et al. . |
| 4,773,404 | 9/1988 | Townsend ...................... 602/26 X |
| 4,817,588 | 4/1989 | Bledsoe . |
| 4,821,707 | 4/1989 | Audette . |
| 4,962,760 | 10/1990 | Jones . |
| 5,002,045 | 3/1991 | Spademan . |
| 5,009,223 | 4/1991 | DeFonce ........................ 602/26 X |
| 5,031,606 | 7/1991 | Ring, Sr. ...................... 602/26 X |
| 5,052,379 | 10/1991 | Airy et al. ........................ 602/16 |
| 5,074,290 | 12/1991 | Harris et al. .................. 602/26 X |
| 5,107,824 | 4/1992 | Rogers et al. ................ 602/26 X |
| 5,230,696 | 7/1993 | Silver et al. .................. 602/26 X |
| 5,286,250 | 2/1994 | Meyers et al. ................ 602/26 X |

FOREIGN PATENT DOCUMENTS 2136294 9/1984 United Kingdom .

*Primary Examiner*—Richard J. Apley
*Assistant Examiner*—Linda C. M. Dvorak
*Attorney, Agent, or Firm*—Townsend and Townsend Khourie and Crew

[57] ABSTRACT

An orthopedic brace, specifically for a knee, has an antifriction mechanical joint to provide easier movement and has the ability of being custom made for different geometries of rotational movements and ranges. The antifriction mechanical joint has a first bearing plate and a second bearing plate which mate with bearing surfaces of a link. The bearing plates each have a cavity therein and a cam rests in each cavity and is attached to each of the bearing surfaces of the link. Rollers fit between the cams and the cavity so when the joint is flexed, there is only rolling movement between the rollers and the contact surfaces of the cams and rollers.

8 Claims, 2 Drawing Sheets

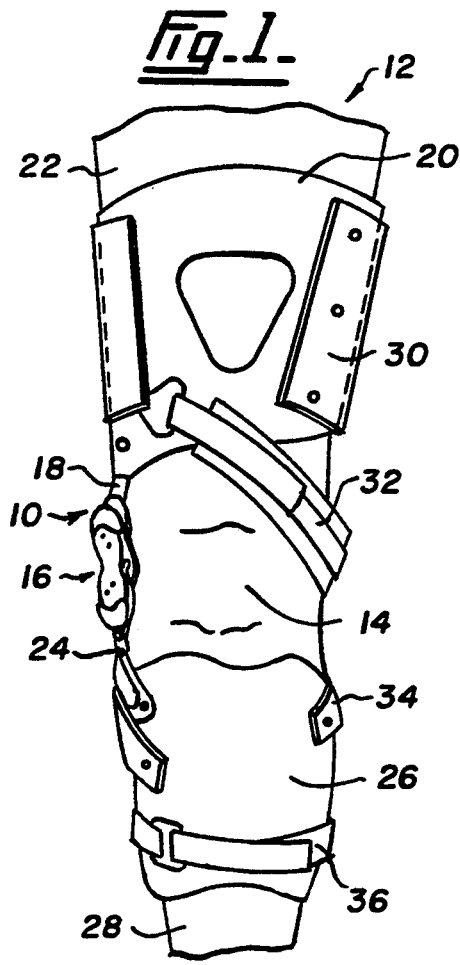
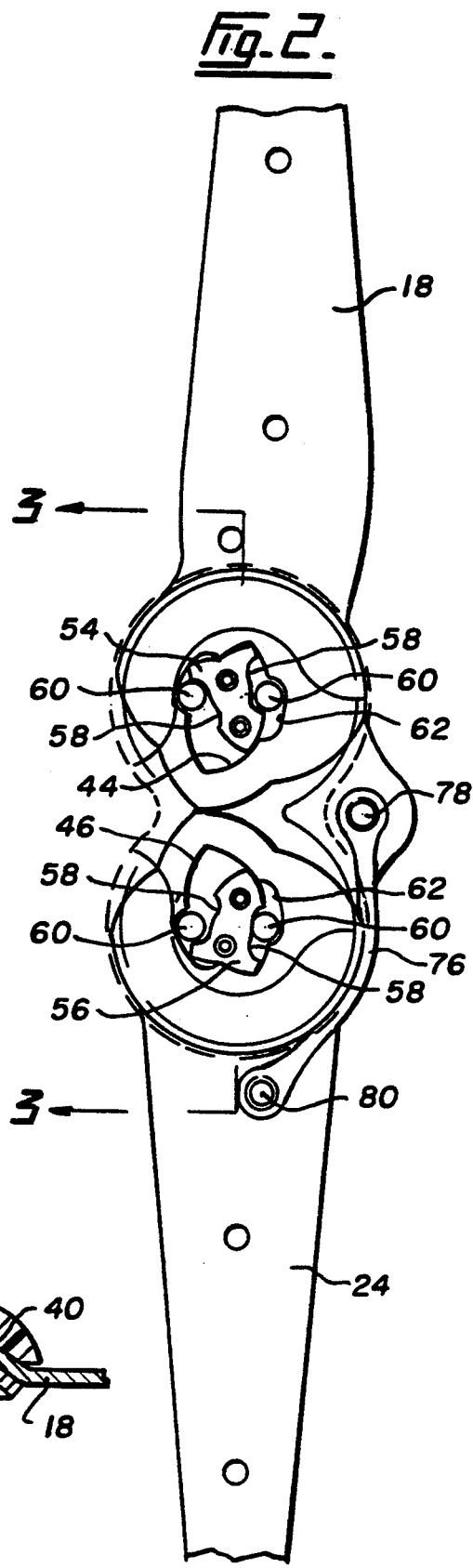
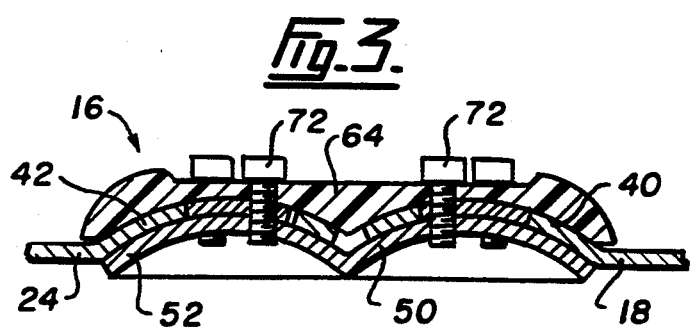

ANTIFRICTION MECHANICAL JOINT FOR AN ORTHOPEDIC KNEE BRACE

TECHNICAL FIELD

The present invention relates to orthopedic braces or prosthetics and more particularly to an antifriction mechanical joint for such braces.

BACKGROUND ART

Orthopedic braces are worn to lend support to a wearer for an injured or weakened joint such as a knee, shoulder, hip, elbow or ankle. Such braces provide support on either side of the joint so that the pivotal action of the joint occurs in a natural manner or as natural as possible. This natural manner permits muscles and ligaments to mend and strengthen.

Leg braces, particularly knee braces, have two arms with a mechanical joint between the arms. The mechanical joint is designed for multiple axis pivotal movement resembling the knee action as closely as possible.

One example of a mechanical joint for an orthopedic brace is disclosed in U.S. Pat. No. 3,902,482 which shows an orthopedic brace having arms attached to a wearer's body on opposite sides of a knee joint. There is a mechanical joint comprising a bearing plate on an end of each brace portion near the body joint and a link extending across the body joint has two bearing surfaces, one at each end, on which the bearing plates rest. The pivot connection between the bearing plates and the link provides a multiple axis pivotal movement as close as possible to the natural pivotal movement of the body joint.

The multiple axis pivotal movement of the brace disclosed in U.S. Pat. No. 3,902,482 results from two curved slots in the bearing plates with pins that extend through the slots and are attached to the two bearing surfaces of the link. It has been found that this brace has achieved excellent acceptance, because it takes up little space, is light and seemingly simple in construction and furthermore follows the relative complex motion of the knee unlike the braces that preceded it. However, the pin and slot operation of the pivot connection tends to wear and in some cases has a restricted or frictional movement when the slots are dragged across the pins as the mechanical joint moves between the flexed position and the extended position of the knee joint.

DISCLOSURE OF THE INVENTION

It is an aim of the present invention to provide an orthopedic knee joint similar in construction to that in U.S. Pat. No. 3,902,482 but having an antifriction mechanical joint to allow for significantly smoother movement between the flexed position and the extended position.

It is a further aim to provide cylindrical rollers similar to the type of rollers used in antifriction roller bearings and thus provide rolling movement rather than sliding movement in the mechanical joint of a knee brace.

It is a further aim to provide an antifriction mechanical joint which utilizes cams fixed to each of the bearing surfaces of the link, the cams having external peripheral surfaces on which at least two cylindrical rollers rest, and wherein the upper arm and lower arm of the knee brace each have bearing plates with a cavity therein, the cavity having curved internal surfaces which engage the cylindrical rollers, thus movement of the bearing plates on the bearing surfaces of the link results in the rollers rotating between the external peripheral surfaces of the cams and the internal surfaces of the cavity in the bearing plates. By changing the shape of the cam and by changing the shape of the cavity, one is able to change the geometry of the multiple axis pivotal movement, and provide more or less flexing as desired. This permits knee braces to be custom made for patients with different ranges of movement between a flexed position and an extended position. By this arrangement one can vary the angle and range of movement as well as the geometry of movement to suit each wearer.

The present invention provides in an orthopedic knee brace having an upper arm to be secured to a wearer's body above the knee, a lower arm to be secured to the wearer's body below the knee, and a mechanical joint between the upper arm and the lower arm to permit flexing of the knee, the improvement of an antifriction mechanical joint comprising: a first bearing plate on an end of the lower arm and a second bearing plate on an end of the upper arm; a link having a first bearing surface to mate with the first bearing plate, and adjacent thereto a second bearing surface to mate with the second bearing plate; thus providing a first bearing at the first bearing plate and a second bearing at the second bearing plate; a first cavity having curved internal surfaces in the first bearing plate and a second similar cavity in the second bearing plate; a first cam having curved external peripheral surfaces fitted within the first cavity and a second similar cam fitted within the second cavity, the cams attached to the link; at least two cylindrical rollers in the first cavity and in the second cavity, the rollers fitting between the internal surfaces of the cavities and the external peripheral surfaces of the cams, the shape of the cams and the shape of the cavities permitting multiple axis pivotal movement of the mechanical joint substantially corresponding to the knee movement of the wearer between a flexed position and an extended position of the knee, and cover means over the first bearing plate and the second bearing plate attached to the link to retain the rollers within the cavities.

BRIEF DESCRIPTION OF DRAWINGS

In drawings which illustrate embodiments of the present invention,

FIG. 1 is a front view of a wearer's knee showing an orthopedic knee brace according to one embodiment of the present invention, FIG. 2 is a side elevation of the antifriction mechanical joint of the knee brace shown in FIG. 1, FIG. 3 is a sectional view taken at line 3—3 of FIG. 2.

BEST MODE FOR CARRYING OUT THE INVENTION

Figure 4:
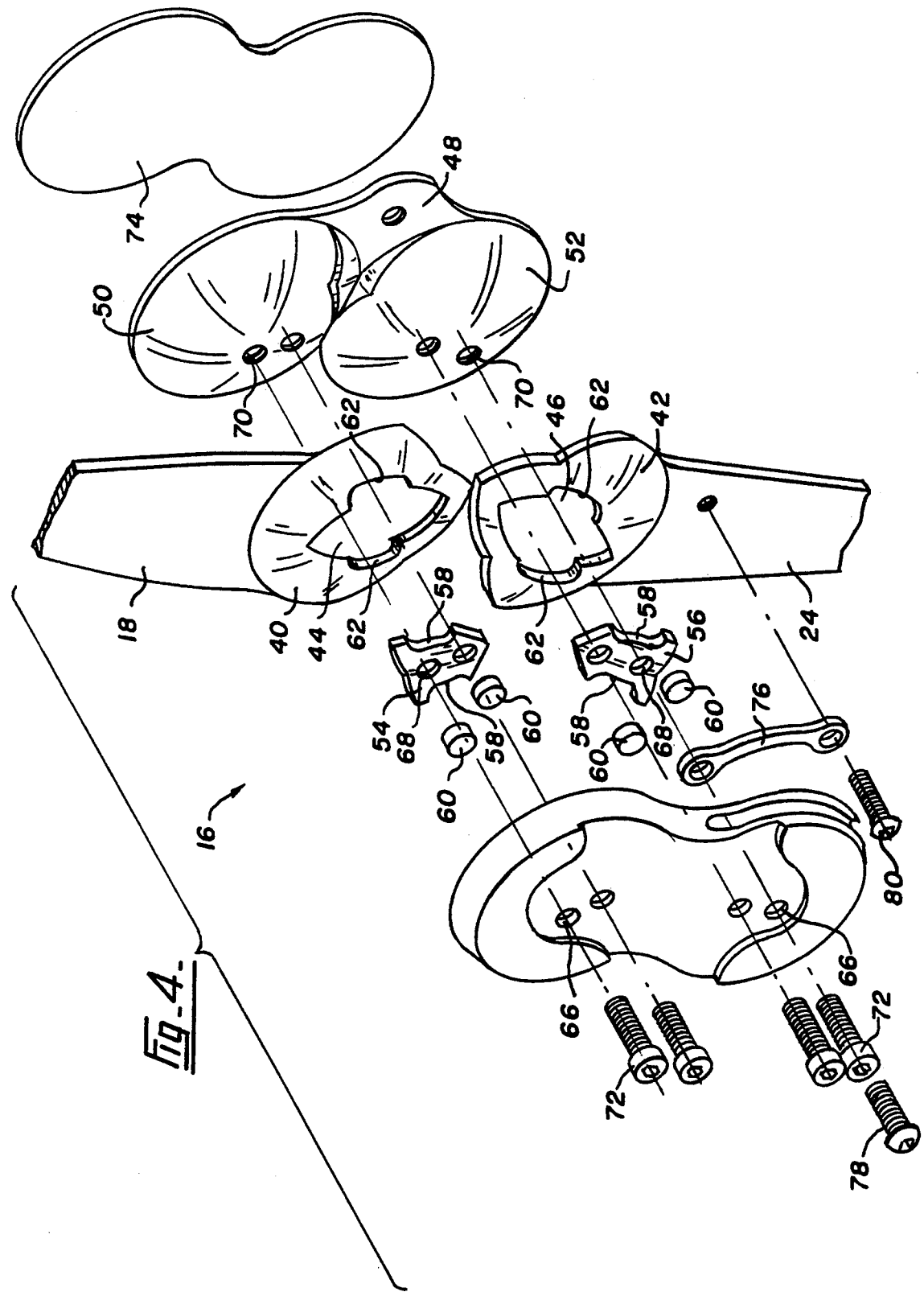
FIG. 4 is an exploded view showing the different elements of the antifriction mechanical joint shown in FIGS. 2 and 3.

The orthopedic brace according to the present invention may be used to reinforce anatomical joints such as shoulders, elbows, hips, knees, and ankles, however, the specific embodiment disclosed herein relates to a knee brace and the mechanical joint for the brace has two bearings defined as a first bearing and a second bearing. Each bearing has multiple axis pivotal movement to closely resemble that of a wearer's knee movement. The natural knee joint does not have a single point of pivot but has a multiple axis pivotal movement which moves about as the lower leg moves between a flexed position and an extended position. Furthermore, slight twisting can occur to the lower leg with respect to the upper leg and this must be taken into account for an orthopedic knee brace.

FIG. 1 illustrates an orthopedic knee brace 10 shown attached to a leg 12 so as to support a knee joint 14. The knee brace has a mechanical joint 16 joined to an upper arm 18 which in turn is secured to an upper cuff 20 about an upper leg 22. The mechanical joint 16 is also connected to a lower arm 24 which in turn is joined to a lower cuff 26 about a lower leg 28.

The upper cuff 20 includes a thigh strap 30 extending around the back of the cuff and a cross strap 32 which extends around the back of the knee 14 to connect to the lower cuff 26. The lower cuff 26 itself has an upper strap 34 and a lower strap 36 to hold the cuff firmly in place. The straps locate the cuffs and may also be for the purpose described in co-pending application Ser. No. 934,819 filed Aug. 24, 1992, now U.S. Pat. No. 5,277,698.

The antifriction mechanical joint 16 is illustrated in more detail in FIGS. 2, 3 and 4. The end of the upper arm 18 has a first bearing plate 40 and the end of the lower arm 24 has a second bearing plate 42. These bearings plates 40 and 42 are substantially the same shape, they are curved with a part spherical surface on the inside, which is adjacent a wearer's knee. The first bearing plate 40 has a first cavity or cutout 44 and the second bearing plate 42 has a second cavity or cutout 46. These cavities are specifically shaped and contoured for rollers to rotate about cam surfaces and permit multiple axis pivotal movement. Behind the first bearing plate 40 and second bearing plate 42 is a link 48 which has a first part spherical bearing surface 50 to match the part spherical surface of the first bearing plate 40 and a second part spherical bearing surface 52 to match the part spherical surface of the second bearing plate 42.

The part spherical surfaces of the first bearing plate 40 and the second bearing plate 42 and the first bearing surface 50 and second bearing surface 52 of the link 48 are preferably coated with an antifriction nonstick surface, such as that sold under the trade mark TEFLON, to provide smooth easy movement between the surfaces with little or no constriction.

A first cam 54 fits in the first cavity 44 and a second cam 56 fits within the second cavity 46. The cams 54 and 56 are illustrated as being substantially arrow shaped and have curved indents 58 on each side for insertion of cylindrical rollers 60, two rollers to each cam fitting within the curved indents 58 rotating about the external peripheral surfaces. The rollers 60 also contact and rotate about the interior surfaces of the cavities 44 and 46 as illustrated in FIG. 2. As can be seen, the curved indents 58 in the cams are positioned opposite curved indents 62 in the cavities 44 and 46. The rotational movement for each bearing is dependent upon the dimensions of the curved indents 58 in the cams 56 and the curved indents 62 in the cavities 44 and 46. The rollers 60 provide rotational movement between the surfaces rather than sliding movement. Variations in the shapes of these curved indents can result in different geometries of rotation and also a difference in the range of multiple axis pivotal movement for each of the two bearings. Whereas the drawings illustrate the cams 56 being substantially the same for the first bearing and second bearing, nevertheless, the shape of cams 56 and the shape of the cavities 44 and 46 may be varied to custom fit a knee brace as desired.

A cover 64 fits over the top of the first bearing plate 40 and the second bearing plate 42. Two holes 66 in the cover align with two holes 68 in each of the cams 54,56 and with two tapped holes 70 in the first bearing surface 50 and two tapped holes 70 in the second bearing surface 52. Machine screws 72 hold the cover 64 the cams 54,56 and the link 48 together as illustrated in FIG. 3. Four machine screws 72 are shown but two are sufficient, one in each cam 54 and 56, with a corresponding reduction in the number of holes 66, 68 and 70.

The cams 54 and 56 may be formed integrally with the surfaces 50 and 52 respectfully.

Sufficient space is provided between the cover 64 and the link 48 so that movement of the first bearing plate 40 and the second bearing plate 42 can take place relative to the link 48. An internal cover pad 74 is provided on the inside of the link 48. This may be padded to protect a wearer's leg.

An elastic member 76 extends from a first anchor bolt 78 attached to the link 48 to a second anchor bolt 80 attached to the lower arm 24. The elastic member tends to urge the second bearing from a flexed position to an extended position. The elastic member 76 eliminates anterior-posterior movement of the lower parts of the brace (24 and 42) relative to the upper parts (18 and 40).

The brace may be of steel but plastic is preferred for ease of production by moulding. The interior surfaces of the cavities 44 and 46 may be inserts to facilitate a precise shape and thus to provide smooth rotating movement as the antifriction rollers rotate. The cylindrical rollers may be formed of hardened steel to better resist wear.

Various changes may be made to the embodiments shown herein without departing from the scope of the present invention which is limited only by the following claims.

The embodiments of the present invention in which an exclusive property or privilege is claimed are defined as follows:

1. In an orthopedic knee brace having an upper arm to be secured to a wearer's body above the knee, a lower arm to be secured to the wearer's body below the knee, and a mechanical joint between the upper arm and the lower arm to permit flexing of the knee, an improved antifriction mechanical joint comprising:
   a first bearing plate on an end of the lower arm and a second bearing plate on an end of the upper arm;
   a link having a first bearing surface to mate with the first bearing plate, and adjacent thereto a second bearing surface to mate with the second bearing plate, thus providing a first bearing at the first bearing plate and a second bearing at the second bearing plate;
   a first cavity having curved internal surfaces in the first bearing plate and a second cavity having curved internal surfaces in the second bearing plate;
   a first cam having curved external peripheral surfaces within the first cavity and a second cam within the second cavity, the cams having curved external peripheral surfaces attached to the link;
   at least two cylindrical rollers in the first cavity and in the second cavity, the rollers fitting between the internal surfaces of the cavities and the external peripheral surfaces of the cams, the shape of the cams and the shape of the cavities permitting multiple axis pivotal movement of the mechanical joint substantially corresponding to the knee movement of the wearer between a flexed position and an extended position of the knee, and cover means over the first bearing plate and the second bearing plate attached to the link to retain the rollers within the cavities.

2. The orthopedic knee brace according to claim 1 wherein the first bearing plate and the second bearing plate have part spherical surfaces and the first bearing surface and the second bearing surface of the link have part spherical surfaces to mate within the part spherical surfaces of the first bearing plate and the second bearing plate.

3. The orthopedic knee brace according to claim 2 wherein the first bearing surface and the second bearing surface of the link and the part spherical surfaces of the first bearing plate and the second bearing plate are coated with antifriction material.

4. The orthopedic knee brace according to claim 1 wherein the cylindrical rollers rotate between curved indents in the first cavity and the first cam, and between curved indents in the second cavity and the second cam.

5. The orthopedic knee brace according to claim 1 wherein the cylindrical rollers are formed of hardened steel.

6. The orthopedic knee brace according to claim 1 including machine screws to hold the cover, the first and second cams and the link together to prevent the first and second cams moving relative to the link.

7. The orthopedic knee brace according to claim 1 wherein the cover is made of a plastic material.

8. The orthopedic knee brace according to claim 1 including an elastic member for the second bearing extending from a first anchor point on the link to a second anchor point on the lower arm, whereby the lower arm is urged from a flexed position to an extended position.

* * * * *